US010814065B2

(12) United States Patent
Fisher et al.

(10) Patent No.: US 10,814,065 B2
(45) Date of Patent: *Oct. 27, 2020

(54) SYRINGE WITH ENERGY DELIVERY COMPONENT AND METHOD OF USE

(71) Applicant: DePuy Synthes Products, Inc., Raynham, MA (US)

(72) Inventors: Michael Alan Fisher, Lawrenceville, GA (US); Chris Mickiewicz, Bridgewater, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 478 days.

This patent is subject to a terminal disclaimer.

(21) Appl. No.: 15/860,714

(22) Filed: Jan. 3, 2018

(65) Prior Publication Data

US 2018/0177950 A1 Jun. 28, 2018

Related U.S. Application Data

(63) Continuation of application No. 11/626,996, filed on Jan. 25, 2007, now Pat. No. 9,895,494.

(51) Int. Cl.
*A61M 5/315* (2006.01)
*A61B 17/88* (2006.01)
(Continued)

(52) U.S. Cl.
CPC ..... *A61M 5/31511* (2013.01); *A61B 17/8836* (2013.01); *G01N 21/31* (2013.01); *A61B 17/22004* (2013.01); *A61B 2017/22014* (2013.01); *A61C 5/62* (2017.02); *A61C 5/64* (2017.02); *A61F 2002/465* (2013.01); *A61F 2002/4688* (2013.01); *A61M 5/001* (2013.01); *A61M 5/007* (2013.01); *A61M 5/445* (2013.01);
(Continued)

(58) Field of Classification Search
CPC .......... A61B 17/22004; A61B 17/8836; A61B 2017/22014; A61C 5/62; A61C 5/64; A61F 2002/465; A61F 2002/4688; A61M 2005/3125; A61M 2005/3306; A61M 2005/50; A61M 5/001; A61M 5/007; A61M 5/31511; A61M 5/445; G01N 21/31; G01N 21/645; G01N 21/76
See application file for complete search history.

(56) References Cited

U.S. PATENT DOCUMENTS 2,693,184 A 11/1954 Lockhart
2,837,092 A 6/1958 Schuller et al.
(Continued)

FOREIGN PATENT DOCUMENTS

JP 2003235968 A 8/2003

OTHER PUBLICATIONS

[No Author Listed] Configure—Merriam Webster Dictionary. Accessed online. Feb. 29, 2016.
(Continued)

*Primary Examiner* — Michael T Rozanski
(74) *Attorney, Agent, or Firm* — Nutter McClennen & Fish LLP

(57) ABSTRACT

A syringe having an energy source disposed therein is disclosed. The syringe is capable of both the delivery and/or aspiration of materials as well as the delivery of an effective amount of various types of energy to a target to produce a desired result. A method utilizing the syringe to administer materials and to deliver energy to the material is also disclosed.

18 Claims, 9 Drawing Sheets

(51) Int. Cl.
  *G01N 21/31*   (2006.01)
  *A61M 5/31*    (2006.01)
  *A61M 5/44*    (2006.01)
  *A61M 5/00*    (2006.01)
  *A61F 2/46*    (2006.01)
  *A61B 17/22*   (2006.01)
  *A61C 5/64*    (2017.01)
  *A61C 5/62*    (2017.01)
  *G01N 21/76*   (2006.01)
  *G01N 21/64*   (2006.01)

(52) U.S. Cl.
  CPC .............. *A61M 2005/3125* (2013.01); *A61M 2205/3306* (2013.01); *A61M 2205/50* (2013.01); *G01N 21/645* (2013.01); *G01N 21/76* (2013.01)

(56) References Cited

U.S. PATENT DOCUMENTS

| | | | |
|---|---|---|---|
| 2,907,328 A | 10/1959 | Cohen | |
| 3,448,277 A | 6/1969 | Jayko | |
| 3,865,548 A | 2/1975 | Padawer | |
| 4,030,499 A | 6/1977 | Bucalo | |
| 4,265,618 A | 5/1981 | Herskovitz et al. | |
| 4,439,197 A | 3/1984 | Honda et al. | |
| 4,732,162 A | 3/1988 | Martell | |
| 4,790,823 A | 12/1988 | Charton et al. | |
| 4,899,910 A | 2/1990 | Tabei et al. | |
| 5,030,216 A | 7/1991 | Theeuwes et al. | |
| 5,108,927 A | 4/1992 | Dorn | |
| 5,155,965 A | 10/1992 | Tabei et al. | |
| 5,222,362 A | 6/1993 | Maus et al. | |
| 5,240,322 A | 8/1993 | Haber et al. | |
| 5,263,323 A | 11/1993 | Maus et al. | |
| 5,279,608 A | 1/1994 | Cherif Cheikh | |
| 5,304,128 A | 4/1994 | Haber et al. | |
| 5,425,713 A | 6/1995 | Taylor et al. | |
| 5,505,706 A | 4/1996 | Maus et al. | |
| 5,528,923 A | 6/1996 | Ledez et al. | |
| 5,749,968 A | 5/1998 | Melanson et al. | |
| 5,823,993 A | 10/1998 | Lemelson | |
| 5,941,897 A | 8/1999 | Myers | |
| 6,006,583 A | 12/1999 | Hayashi | |
| 6,210,368 B1 | 4/2001 | Rogers | |
| 6,402,734 B1 | 6/2002 | Weiss | |
| 6,440,748 B1 | 8/2002 | Katerkamp et al. | |
| 6,464,682 B1 | 10/2002 | Snoke | |
| 6,542,350 B1 | 4/2003 | Rogers | |
| 6,685,678 B2 | 2/2004 | Evans et al. | |
| 6,706,011 B1 | 3/2004 | Murphy-Chutorian et al. | |
| 6,706,020 B1 | 3/2004 | Urich et al. | |
| 6,908,460 B2 | 6/2005 | DiStefano | |
| 6,925,323 B2 | 8/2005 | Snoke | |
| 6,966,894 B1 | 11/2005 | Urich et al. | |
| 7,699,834 B2 | 4/2010 | Hood et al. | |
| 7,749,447 B1 | 7/2010 | Sauter, Jr. | |
| 7,896,868 B2 | 3/2011 | Hood et al. | |
| 7,914,499 B2 | 3/2011 | Gonnelli et al. | |
| 7,942,867 B2 | 5/2011 | Hood et al. | |
| 8,109,923 B2 | 2/2012 | Hood et al. | |
| 8,672,883 B2 | 3/2014 | Denning et al. | |
| 9,895,494 B2 | 2/2018 | Fisher et al. | |
| 2001/0056258 A1 | 12/2001 | Evans | |
| 2002/0055712 A1 | 5/2002 | Neracher | |
| 2004/0064101 A1 | 4/2004 | Kowan et al. | |
| 2004/0158205 A1 | 8/2004 | Savage | |
| 2004/0254533 A1 | 12/2004 | Schriver et al. | |
| 2005/0080384 A1 | 4/2005 | Green | |
| 2005/0154434 A1 | 7/2005 | Simon et al. | |
| 2006/0095137 A1 | 5/2006 | Chung et al. | |
| 2007/0219480 A1 | 9/2007 | Kamen et al. | |
| 2007/0260228 A1 | 11/2007 | O'Dowd et al. | |
| 2007/0299431 A1 | 12/2007 | Jakubowski et al. | |
| 2008/0183122 A1 | 7/2008 | Fisher et al. | |
| 2014/0274825 A1 | 9/2014 | Jones et al. | |
| 2017/0056604 A1 | 3/2017 | Cowan et al. | |

OTHER PUBLICATIONS

U.S. Appl. No. 11/626,996, filed Jan. 25, 2007, Syringe With Energy Delivery Component and Method of Use.

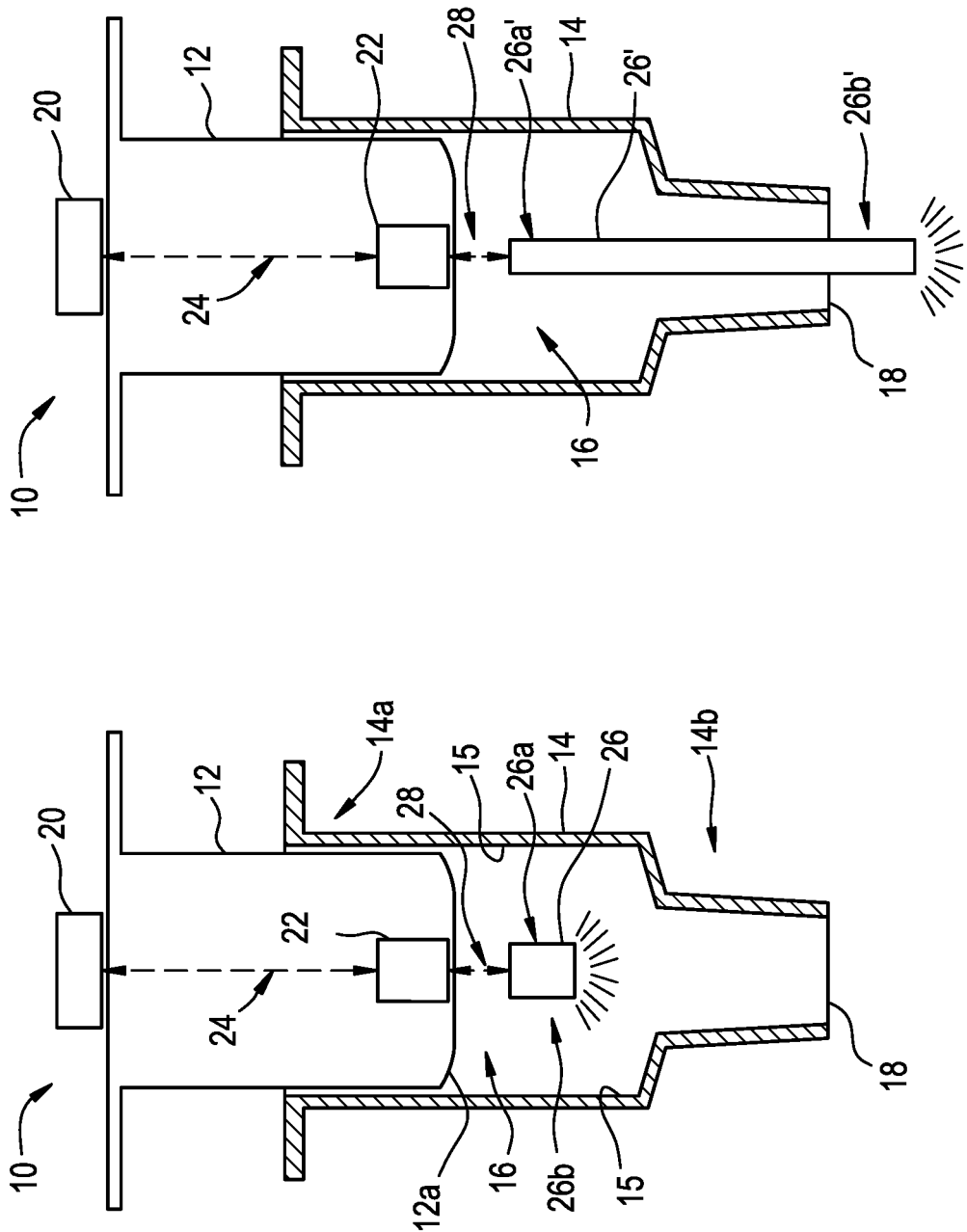

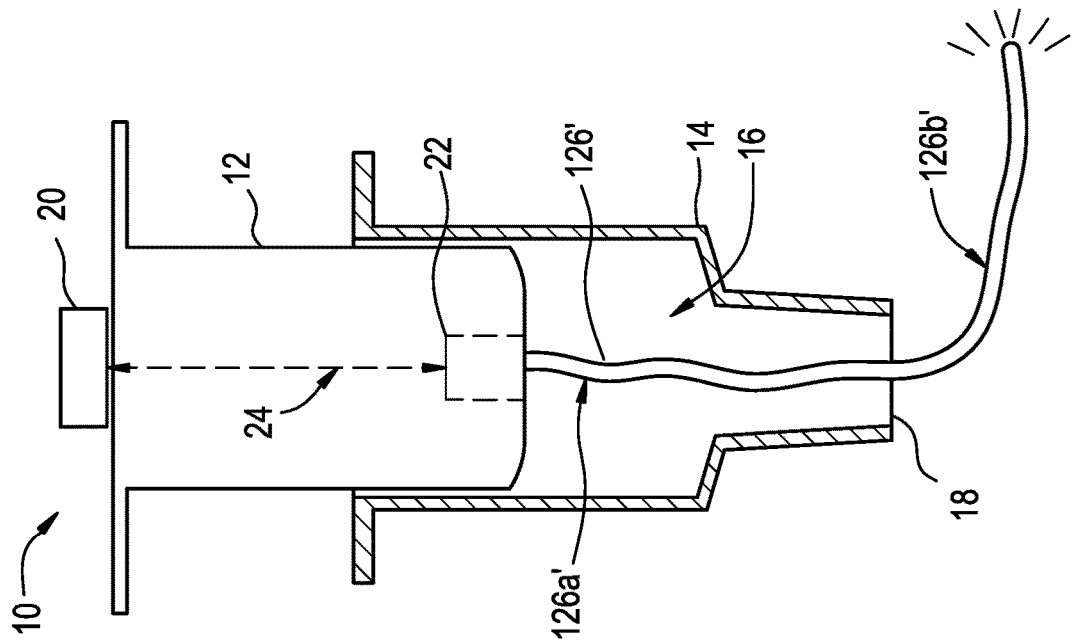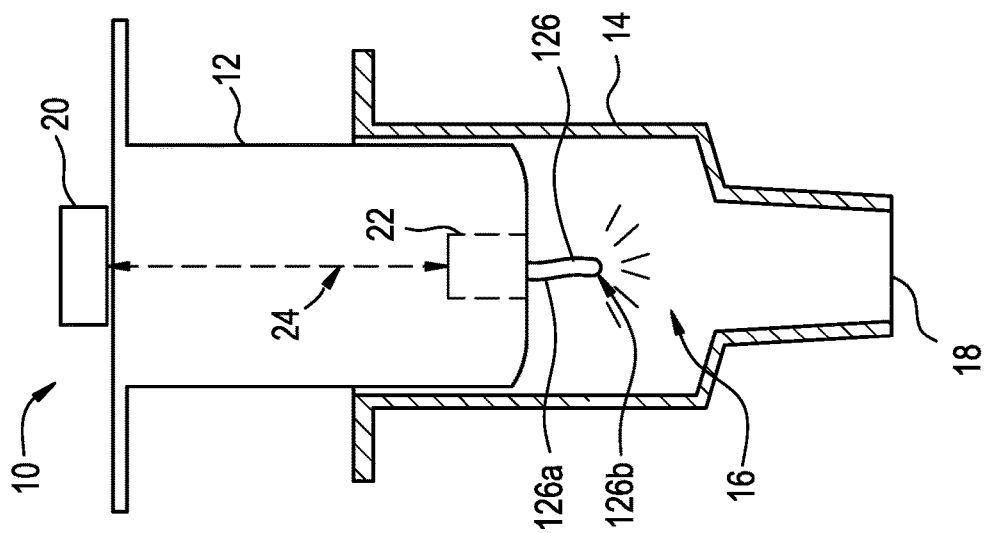

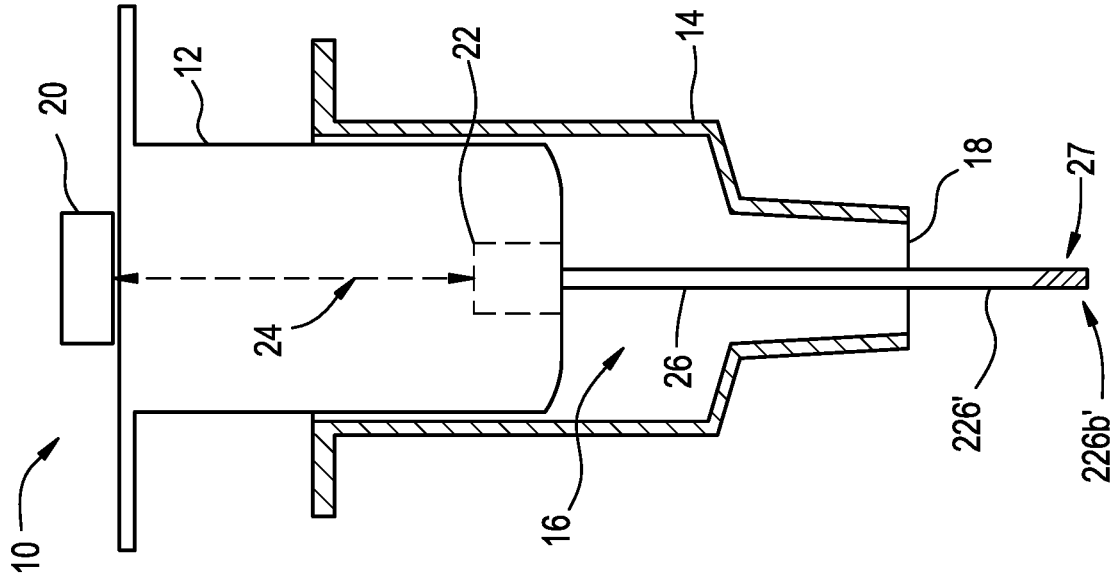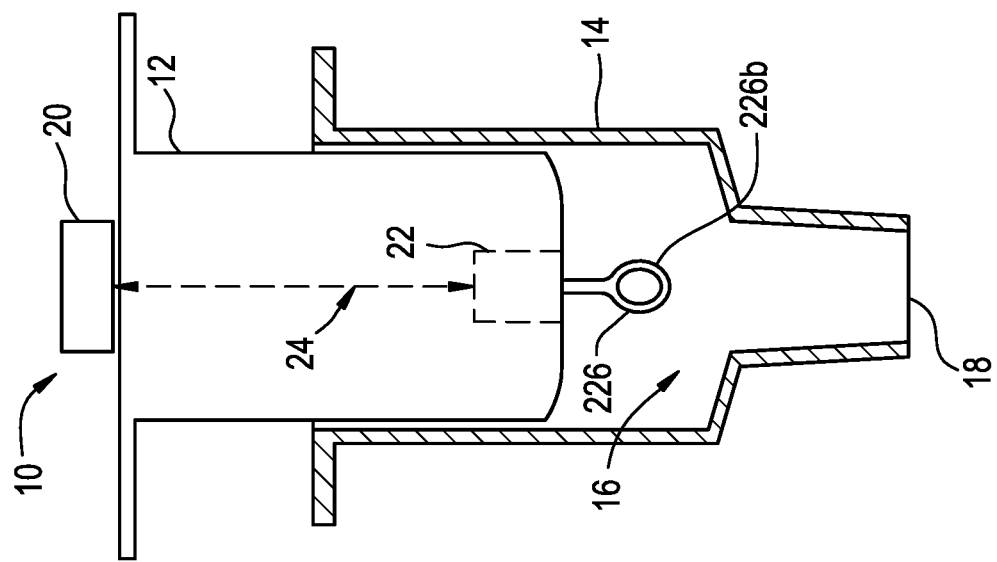

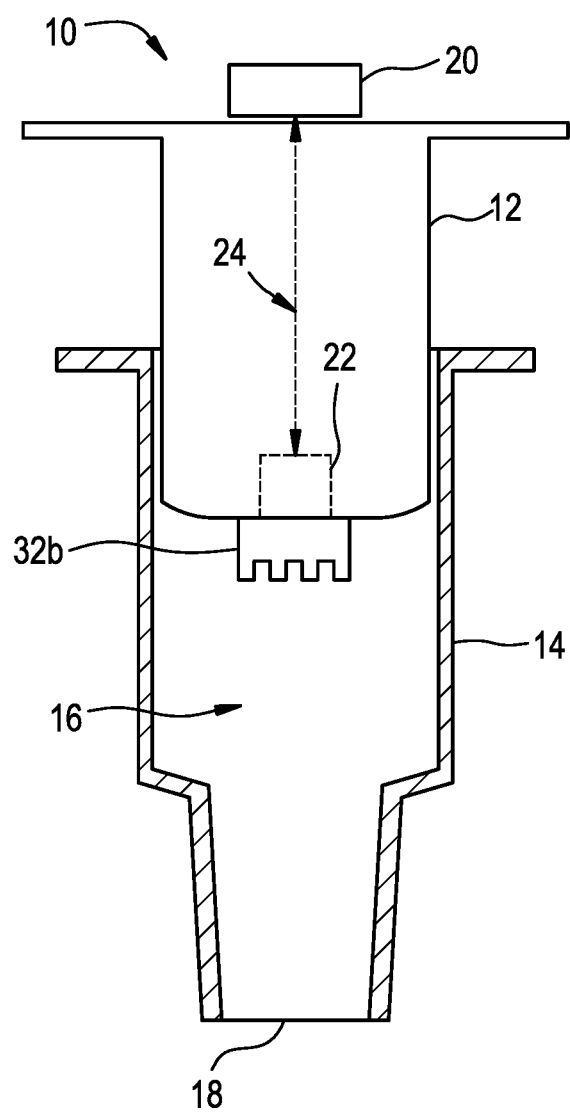

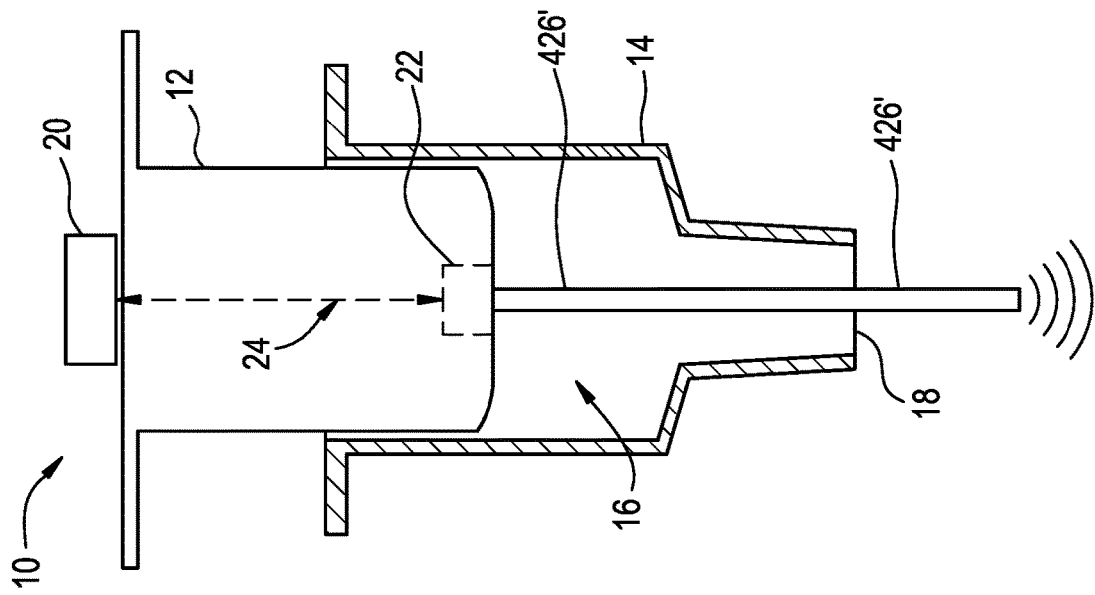
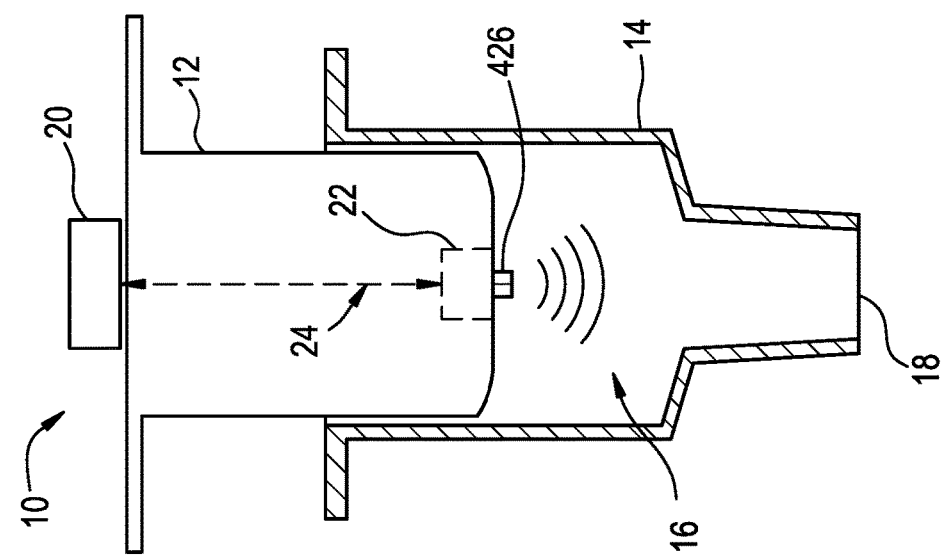

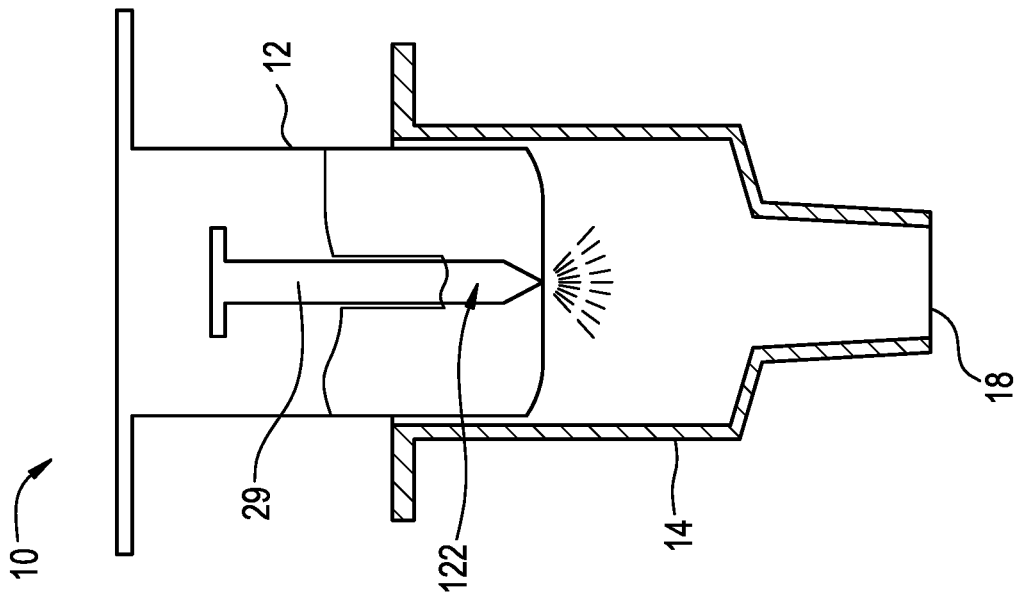
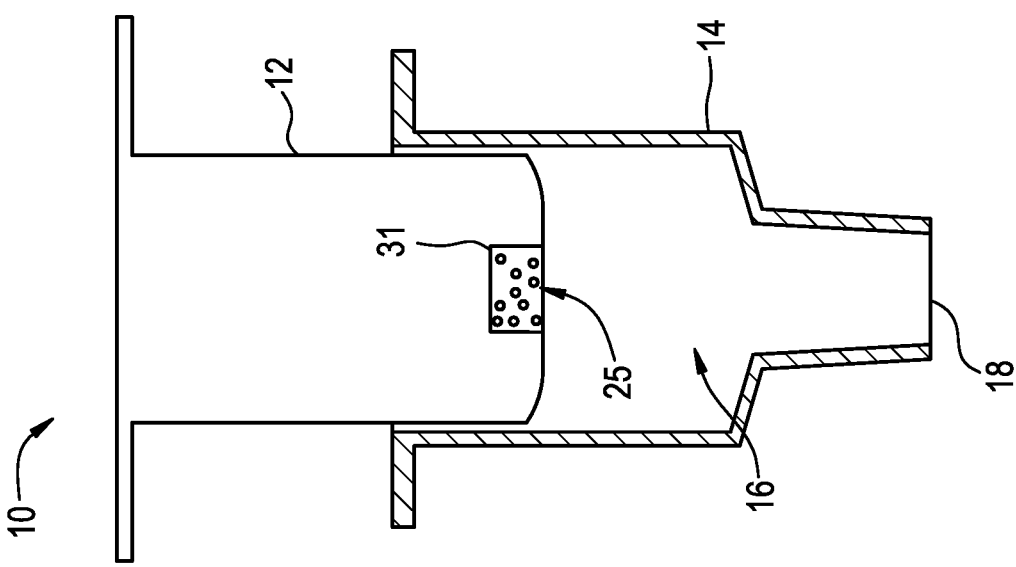

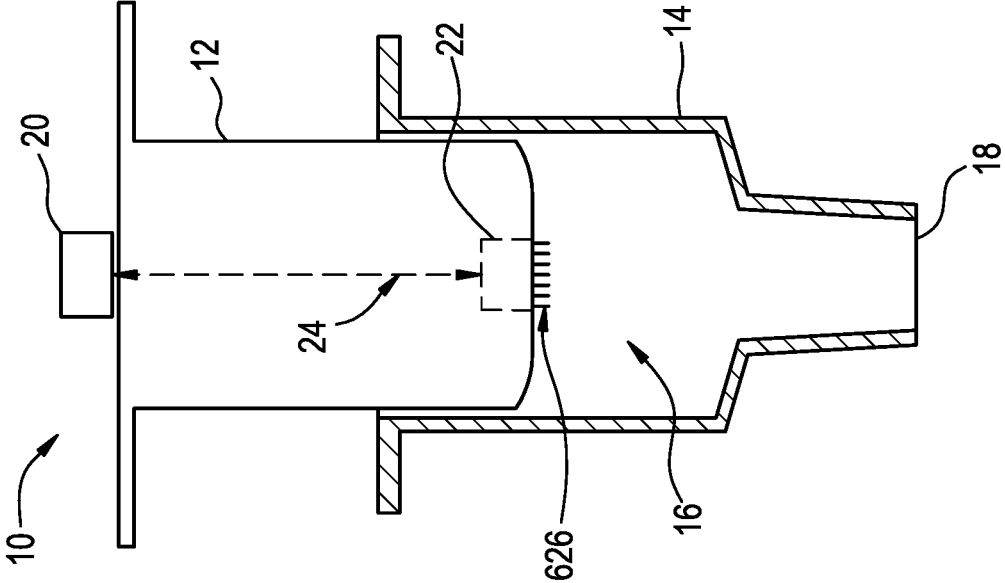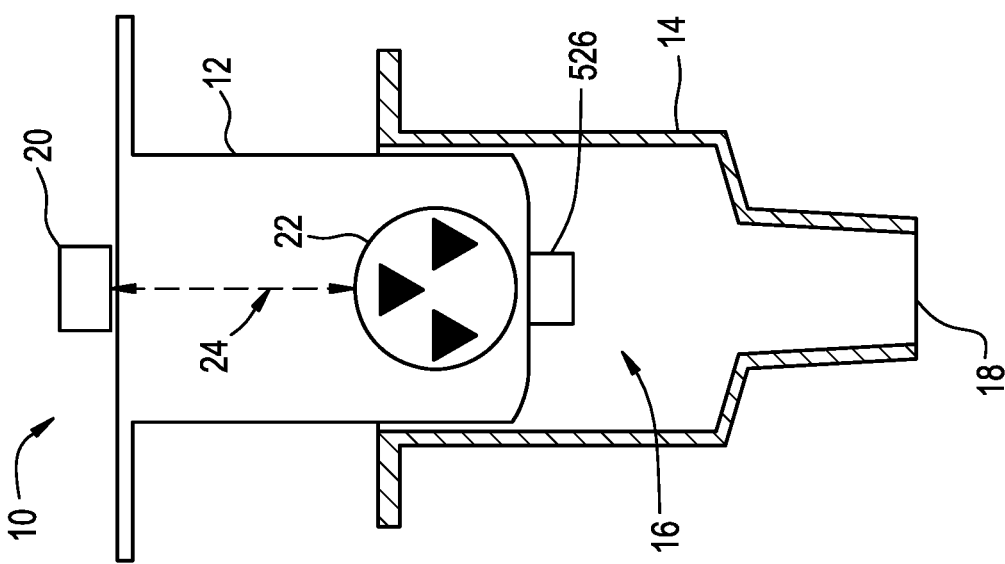

US 10,814,065 B2

SYRINGE WITH ENERGY DELIVERY COMPONENT AND METHOD OF USE

CROSS-REFERENCE TO RELATED APPLICATIONS

This application is a continuation of U.S. application Ser. No. 11/626,996 filed on Jan. 25, 2007, now U.S. Pat. No. 9,895,494, which is hereby incorporated by reference in its entirety.

FIELD OF THE INVENTION

The present invention relates to syringe and syringe-like devices capable of generating and delivering various types of energy to both internal and external targets in order to produce desired effects.

BACKGROUND OF THE INVENTION

Syringes or syringe-like devices are commonly used to aspirate or deliver fluidized materials in medical and technical applications. Some surgical procedures or industrial processes require that energy be delivered to a material in order to activate the material, change the physical and/or chemical properties of the material, identify the state or composition of that material, and/or enhance the material's therapeutic benefits. As examples, photo-polymerizing resins require the addition of light energy after or during delivery to the area of application. Various other materials require the addition of heat either prior to and/or following delivery of the material. Some photodynamic therapies require the delivery of therapeutic materials to biological sites where the materials only have therapeutic actions when exposed to specific types of photonic energy. Additionally, some therapeutics, such as suspensions, need to be agitated prior to being expelled from the syringe in order to maintain the consistency of the suspension (i.e., prevent particles from settling out of solution or suspension.)

Such procedures are typically performed in multiple steps with multiple devices. Commonly, a syringe is used to deliver therapeutic materials to the treatment area and following delivery, the syringe is removed and a second device capable of producing and supplying energy is delivered to the site. These multi-step processes are inefficient, may lead to poor performance due to delay in supplying the necessary energy, and have the potential to deliver the energy to the incorrect location or in the incorrect dosage.

SUMMARY OF THE INVENTION

In one aspect, the invention provides a syringe which includes a barrel having proximal and distal ends. The proximal end of the barrel is configured to accept a piston while the distal end of the barrel includes an outlet for discharging a material from within the barrel. The syringe can also include at least one energy source associated with the syringe and capable of generating energy and a delivery element in communication with the energy source. The delivery element is capable of delivering energy from the energy source to a target to produce a desired effect in the target. The target may be internal and/or external of the device.

The device may include any type of energy source capable of being associated with the syringe, generating an effective amount of energy to produce a desired result, and ultimately transmitting the energy to the desired target. As examples, the energy source may be selected so as to produce energy forms of the type including photonic energy, ultrasonic energy, mechanical energy, chemical energy, electrostatic energy, magnetic energy, radioactive energy, biological energy, thermal energy, nuclear energy, etc.

The delivery element of the device can be any element capable of being in communication with the energy source and transmitting energy to the target. The delivery element can remain positioned within the barrel of the syringe or it can be configured such that a portion of the delivery element can selectively extend through the barrel and out of the syringe to be positioned adjacent to or in direct contact with an external target. Additionally, the delivery element can act as a transducer. Examples of delivery elements may include optical and mechanical waveguides, thermal exchangers, heating coils, mechanical agitators, catalytic surfaces, etc.

Additionally, the syringe may house any type of material required for a desired procedure or process. As one example, the material may be a photopolymerizing resin. As an alternative example, the material may be an aspirated biological sample (water, blood, serum, etc.)

In an alternative embodiment, a detector may additionally be associated within the syringe. A suitable detector is one that is capable of measuring a response (e.g., a reflectance, absorbance, etc.) from the target (e.g., the material) resulting from the delivery of energy.

In a further aspect the present invention also provides a method of treatment comprising delivering a distal end of a syringe to a treatment site and delivering the energy from the energy source to a target through a delivery element, at least a portion of which is disposed within the syringe. According to the method disclosed herein the energy is capable of producing a desired effect in the target. In one aspect, the target is disposed within the syringe and the energy is delivered thereto before the target material is ejected from the syringe. In another embodiment the target is external to the syringe and energy is applied to the target following ejection of the material from the syringe. The energy source can be selected from a variety of energy types, depending on the effect that is to be achieved. For example, the energy type can be selected from the group consisting of ultrasonic energy, radiation energy, thermal energy, and mechanical energy. In another aspect, the method can be conducted to measure a response from the target prior to ejecting the material from the syringe. The response can be measured by a detector disposed in the syringe.

BRIEF DESCRIPTION OF THE DRAWINGS

The invention will be more fully understood from the following detailed description taken in conjunction with the accompanying drawings, in which:

FIG. 1A is a representation of a general embodiment of the device being capable of generating and delivering energy to an internal target;

FIG. 1B is a representation of a general embodiment of the device being capable of generating and delivering energy to an external target;

FIG. 2A is a representation of an embodiment of the device being capable of generating and delivering light energy to an internal target;

FIG. 2B is a representation of an embodiment of the device being capable of generating and delivering light energy to an external target;

FIG. 3A is a representation of an embodiment of the device being capable of generating and delivering mechanical energy to an internal target;

FIG. 3B is a representation of an embodiment of the device being capable of generating and delivering mechanical energy to an external target;

FIG. 4 is a representation of an embodiment of the device being capable of delivering heat energy to an internal target;

FIG. 5A is a representation of an embodiment of the device being capable of generating and delivering ultrasonic energy to an internal target;

FIG. 5B is a representation of an embodiment of the device being capable of generating and delivering ultrasonic energy to an external target;

FIG. 6A is a representation of an embodiment of the device being capable of delivering a biological material to an internal target in order to produce a desired effect;

FIG. 6B is a representation of an embodiment of the device being capable of delivering a chemical to an internal target in order to produce a desired effect;

FIG. 7A is a representation of an embodiment of the device being capable of generating and delivering radioactive energy to an internal target;

FIG. 7B is a representation of an embodiment of the device being capable of removing heat from a fluidized material housed in a barrel of the device;

DETAILED DESCRIPTION OF THE INVENTION

Figure 8A:
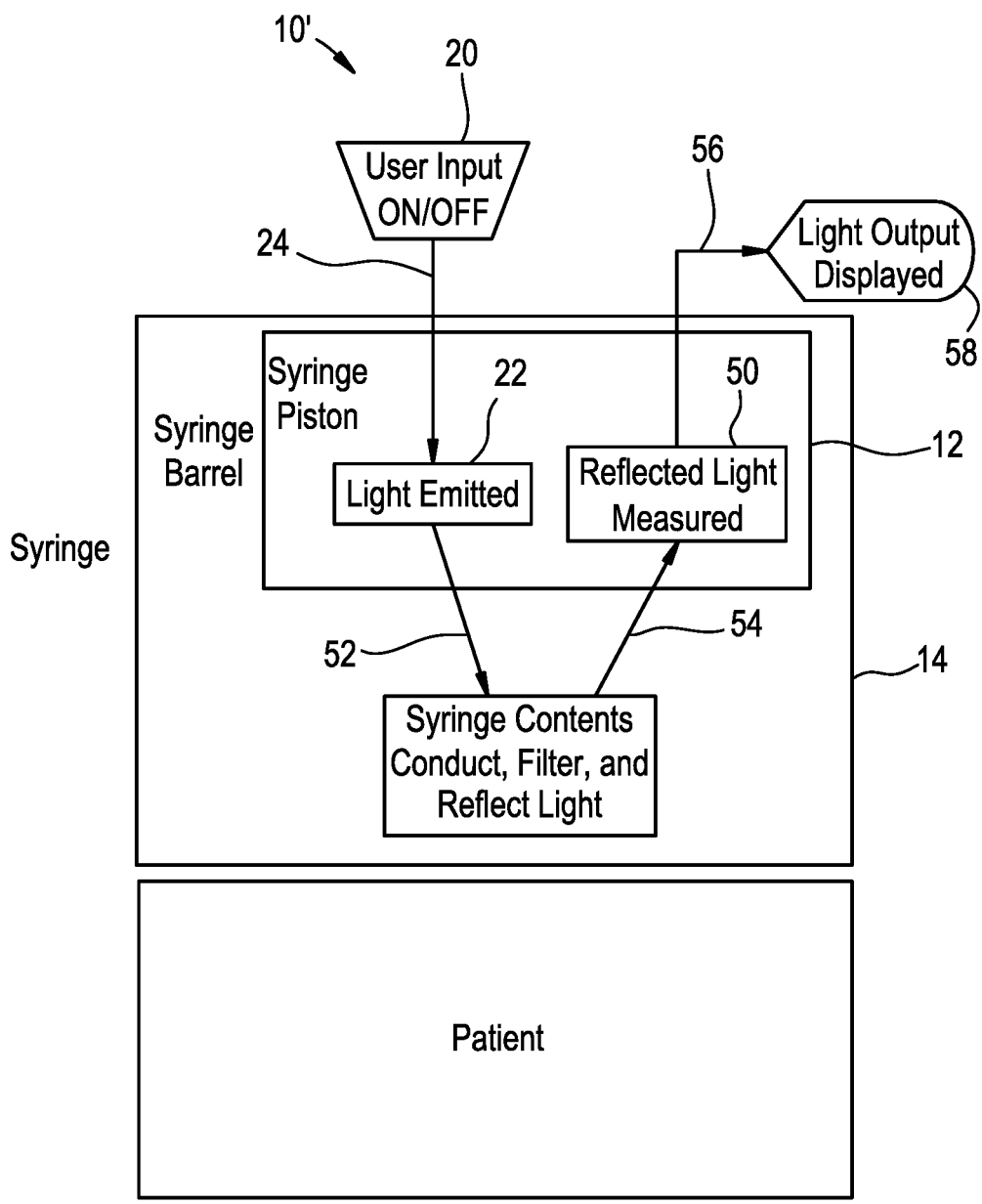
FIG. 8A is a representation of an embodiment of the device being capable of performing an analytical measurement of the material housed in the barrel of the device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In one aspect the invention provides a syringe or syringe-like devices capable of generating and delivering various types of energy to both internal and/or external targets thereby eliminating the need for multiple devices to perform procedures requiring the delivery of both therapeutic materials and energy. The ability to eliminate the need for multiple devices can reduce the number of potential contamination sources, reduce the costs and complexities associated with such procedures, and may significantly improve performance and efficiency by substantially eliminating any delay between the delivery of materials and energy.

Like a typical syringe, the device includes a barrel adapted to receive a piston and capable of aspirating or expelling materials from the barrel to the treatment area. The device further includes an energy source disposed within or associated with the device. The energy source can be coupled to a delivery element, which can be adapted to receive, propagate, and transmit energy to the desired target to produce a desired effect. In one embodiment the target can be the material before and/or after it is expelled from the syringe. Alternatively, the target may be the treatment area itself (e.g., for purposes of roughening or otherwise treating a surface prior to delivery of material such as an adhesive).

As will be discussed in detail below, the device may include any type of energy source capable of being disposed within the syringe, generating energy, coupling to a delivery element, and ultimately transmitting an effective amount of energy to the desired target. The type of energy delivered can vary depending on the purposes of a given treatment. By way of non-limiting example, the energy can be photonic, mechanical, ultrasonic, thermal, magnetic, electrical, nuclear, or radiation energy. The following provides a detailed discussion of the various energy sources, energy types, delivery elements, targets, desired effects, etc. within the scope and spirit of the present invention. Those skilled in the art will appreciate that the following merely provides examples of various embodiments of the device and is in no way meant to limit the scope of the invention. Identical reference numerals are used herein to denote like elements.

FIGS. 1A and 1B provide general overviews of alternative embodiments of the present invention wherein the device 10 is capable of delivering energy to a target internal to the syringe (as shown in FIG. 1A) and to an external target (as shown in FIG. 1B). Referring to FIG. 1A, the device 10 can include a barrel 14 having proximal 14a and distal 14b ends. The proximal end 14a of the barrel 14 can be adapted to receive a piston 12. The piston 12 includes a distal end 12a, which together with the inner walls 15 of the barrel, defines a variable internal volume 16 that is capable of housing a fluidized material. The piston 12 is movably mated to the barrel 14 such that an external force can drive the piston 12 in a distal direction thereby decreasing the internal volume 16 and ultimately expelling the material from the device 10 via an opening 18 positioned at the distal end of the barrel 14. As will be appreciated by those skilled in the art, the various components of the syringe may include any sterilizable biocompatible material commonly used in the art.

The device 10 further includes an energy source 22 that is adapted to deliver energy to any desired target through an energy delivery element 26, 26', as described below. In one embodiment, the energy source 22 may be disposed at any position within the syringe. For example, the energy source 22 can be disposed on, within, or in association with the piston 12. In general, the energy source 22 may include any source capable of being disposed within the device 10 and further capable of generating an effective amount of the type of desired energy. In an exemplary embodiment, the energy source 22 is battery powered or is able to communicate with an AC source.

The energy source 22 of the various embodiments may be selected so as to produce any type of energy necessary to yield the desired effect as required by a procedure. In exemplary embodiments, the energy source 22 may generate and deliver various types and frequencies of light energy (ultraviolet, infrared, etc.), electrical energy (alternating current, direct current, monopolar, bipolar, etc.), magnetic energy, nuclear/radioactive energy, chemical energy, mechanical energy (various frequencies of both longitudinal and rotational), ultrasonic energy (various frequencies and/or types), thermal energy, electrostatic energy, or any combination of the above. Those skilled in the art will appreciate that other types of energy are also within the spirit and scope of the present invention, and that combinations of different energy sources may be present within the same device.

Referring again to FIG. 1A, the energy source 22 can be in communication (as indicated by dashed line 24) with a user input 20, which enables a user to selectively activate/ deactivate the energy source 22. Those skilled in the art will appreciate that various methods may be utilized to establish such communication.

The energy source 22 can be in communication (as indicated by arrow 28) with an energy delivery element 26, 26'. The energy delivery element 26, 26' can be any type of device that is capable of receiving energy from the energy source 22 and ultimately delivering the energy to a target. For example, the delivery element 26, 26' can include a waveguide (optical, mechanical, acoustic, etc), a thermal energy conduit, a mechanical agitator, a thermal coil, etc. In another embodiment, the delivery element 26, 26' can act as an energy transducer wherein the input energy from the energy source 22 can be transformed from one type or kind of energy to another type of kind of energy (e.g., a stainless steel loop that transforms electrical current energy from the energy source 22 to thermal energy via Ohmic resistance within the steel). As will be discussed below, the identity and configuration of the energy delivery element 26, 26' will depend on factors including the type of energy being delivered to the target and the location of the target. Furthermore, the delivery element 26, 26' may be adapted so as to limit the transmission of energy to a portion of the energy delivery element 26, 26' (e.g., the distal tip) or to allow for delivery of energy along any desired length of the energy delivery element 26, 26'. Also, the energy delivery element may be capable of being extended and/or retracted from within the barrel 14 so as to allow the user to deliver energy to various targets during a procedure.

It is understood that the term "communication" is used in its broad sense and encompasses a connection between elements wherein the connection may be effected by optical, electrical (including wireless), physical means, or other forms of connection.

FIG. 1A illustrates an embodiment in which the delivery element 26 remains positioned within the barrel 14 and it is adapted to deliver energy to a target that is internal to the barrel 14 of the syringe. As shown, the energy delivery element 26 includes proximal 26a and distal 26b ends, the proximal end 26a is in communication (as indicated by dashed line 28) with the energy source 22, and the distal end positioned within the internal area 16 of the device 10. For purposes of illustration, the energy delivery source is shown separated from the distal end 12a of the piston, however, one skilled in the art will appreciate that the energy delivery element 26 will have a proximal end 26a that is normally directly connected to the distal end 12a of the piston. As so constructed, the embodiment of FIG. 1A enables energy to be delivered to a material within the barrel 14 before it is expelled from the syringe 10 to initiate or effect some desired chemical and/or physical change in the material.

FIG. 1B is representative of an alternative embodiment that enables the energy delivery element 26' to deliver energy to a target external to the syringe. As shown in FIG. 1B, device 10 is virtually identical to that shown in FIG. 1A, except that it has an energy delivery element 26' that is configured such that at least a portion thereof (e.g., its distal end 26b') can be selectively delivered through the distal opening 18 so that it can be positioned adjacent to or in contact with an external target. In this embodiment, the external target can be the material expelled from the device 10, or the target can be the treatment area itself. Like FIG. 1A, for purposes of illustration, the energy delivery source is shown separated from the distal end 12a of the piston, however, one skilled in the art will appreciate that the energy delivery element 26' normally will have a proximal end 26a' that is directly connected to the distal end 12a of the piston.

Many variations of these general embodiments will be discussed in detail below. As one skilled in the art will appreciate, these general embodiments can be modified and adapted to deliver different forms of energy to different target types. In one variation, the delivery element can deliver energy to a material after the material has been aspirated into the syringe 10. For example, energy can be delivered to a site (or material) external to the syringe, and a material to which the energy is applied can be aspirated. Alternatively, a material can be aspirated and then subject to energy delivery/transduction within the syringe. One skilled in the art will understand the usefulness of the invention described herein in connection with processes (including cellular processing and biological/industrial diagnostics) that involve the aspiration of materials into the syringe barrel.

FIGS. 2A-2B illustrate embodiments in which the energy source 22 is a light energy source. The energy source 22 can be selected so as to produce any frequency and/or type of light energy (e.g., ultraviolet light, infrared light, etc.) as is required to produce a desired effect. One skilled in the art will appreciate that the energy delivery element 126, 126' used for the delivery of light energy may include any element capable of coupling to the energy source 22, propagating light energy along the length, and ultimately delivering light energy to the external target. In exemplary embodiments, the energy delivery element 126, 126' is a fiber optic cable or waveguide.

FIG. 2A illustrates an embodiment that is similar in many ways to the general embodiment of FIG. 1A in that the delivery element 126 is capable of delivering energy to an internal target, such as the therapeutic material, before the material is expelled from barrel 14 of the device 10. The energy delivery element 126 includes proximal and distal ends 126a, 126b wherein the proximal end is in communication with the energy source 22. In this embodiment the distal end 126b of the delivery element 126 is positioned within and remains within the internal volume 16 of the device 10.

FIG. 2B illustrates an embodiment that is similar in many ways to the general embodiment shown in FIG. 1B, except that it is adapted to deliver light energy to a target external to the syringe. As shown in FIG. 2B, the energy delivery element 126' has proximal and distal ends 126a', 126b', and the distal end 126b' can be expelled through the opening 18 in the barrel 16 to position the energy delivery device 126' adjacent to a target material external to the device 10. In an alternative embodiment, the energy delivery element 126' can include two optical wave guides that carry afferent (from the syringe) and efferent photonic energy (to the syringe) thereby enabling the illumination of distal targets and collection of reflected/refracted light for use in spectroscopic analysis of these targets.

Light energy can be supplied to the energy delivery elements 126, 126' to initiate or effect virtually any type of a physical and/or chemical change in the target material that is disposed within or external to the barrel 14. For example, the delivery of light energy can initiate polymerization of a light-activated resin. Alternatively, an ultraviolet ("UV") light energy source may be utilized so as to sterilize and/or deactivate biota contained with the material. In another example, the light may be capable of catalyzing or producing a desired reaction involving the target material. A further example of a chemical and/or physical change that can be effected through the delivery of light energy is the color bleaching of the therapeutic material before or after delivery of the material to the target. As will be discussed in relation to FIGS. 8A-8B, the light energy can also be useful in performing an analytical measurement (e.g., a spectroscopic analysis) prior to expelling the material from the device 10.

Although FIGS. 2A and 2B illustrate light energy being delivered only through a distal end of the energy delivery element, it is understood that the energy delivery element can be configured to deliver light energy delivered along its entire length or any portion thereof.

FIGS. 3A-3B provide examples of embodiments of the device capable of delivering mechanical energy to targets within (FIG. 3A) and outside of (FIG. 3B) the barrel 14. With reference to FIG. 3A, the delivery element 226 can be adapted to deliver mechanical energy of various frequencies and types (e.g., rotational, longitudinal, vibrational, etc.) to the material contained within the syringe 10 before the material is expelled from the syringe 10. In such an embodiment, the distal end 226b of the delivery element 226 remains within the barrel 14 of the syringe 10 and it is configured to provide an agitation/mixing energy to the material. One skilled in the art will appreciate that the delivery element 226 may take any shape in order to produce the desired effect. In an exemplary embodiment, the distal end 226b of the delivery element 226 has a feature, such as a paddle, that is effective to mix and/or agitate the material disposed within the barrel. The effect of delivering such energy may produce and/or maintain a desired viscosity of the material necessary for a procedure or process. Alternatively, the energy can maintain a particulate suspension. For example, in a procedure requiring the injection of a contrast agent, the barrel 14 may contain a saline solution having suspended radioopaque particles. Mechanical agitation of such a therapeutic material may help to maintain the particulate suspension and can improve the subsequent delivery of the material.

FIG. 3B illustrates an alternative embodiment wherein the energy delivery element 226' is able to be selectively extended out through the opening 18 in the barrel to be positioned adjacent to or in direct contact with an external target. As shown, the energy delivery element 226' is in communication with the mechanical energy source 22 and extends from the distal end 12a of the plunger. Like the embodiment of FIG. 3A, the distal end 226b' of the energy delivery element 226' may include features such as threads and/or protrusions 27 that can enhance or facilitate the delivery of mechanical energy. Alternatively, the feature at the distal end 226b' may be shaped as a paddle or another object that can facilitate delivery of a mixing/agitating energy to the target. As discussed above, the target may be the therapeutic material after it has been expelled from the barrel 14. In another example, the external target may be the treatment area itself, such as a surface that can be roughened in preparation for the delivery of an agent such as an adhesive polymer.

FIG. 4 is an example of the device 10 wherein the energy source 22 and delivery element 326 are selected to deliver an effective amount of thermal energy to the material before the material is expelled from the device 10. In such an embodiment, the delivery element 326 may be any element capable of being in communication with the thermal energy source 22 (e.g., any type of thermal mass, thermal generator, resistance heater, etc.) and capable of transmitting heat to the target material. In an exemplary embodiment, the delivery element 326 is a heating coil. As is known to those skilled in the art, delivery of thermal energy to the material may produce various desired effects including improving the flowability of the material, triggering a curing process, and/or catalyzing or initiating in a desired reaction. Although not shown, the delivery element may be adapted to deliver thermal energy to external targets such as the expelled material and/or the external treatment site in order to produce a desired effect.

FIGS. 5A and 5B show additional representations of embodiments of the device 10 wherein the energy source 22 and delivery element 426 are selected in order to deliver any frequency and/or type of ultrasonic energy to various internal (FIG. 5A) and/or external (FIG. 5B) targets in order to produce desired effects. With reference to FIG. 5A, the energy delivery element 426 can include any element capable of coupling to the energy source 22 and transmitting ultrasonic energy to the material. By way of non-limiting example, the delivery element 426 can be a wave guide, a piezoelectric material, an oscillating beam, or a tuning fork. Similar to the embodiments discussed above, ultrasonic energy may be delivered to the material in order to produce any effect as required by a given procedure.

In the embodiment of FIG. 5B, the delivery element 426' can be adapted to deliver an effective amount of ultrasonic energy to an external target.

FIG. 6A is a representation of an alternative embodiment of the device wherein the delivery element 25 can house an energy source in the form of a swatch or culture of biological agents 31 (e.g., cells, bacteria, yeast or viruses) capable of being delivered to the material. When introduced to the material, the biological agents 31 are capable of producing some useful form of action or reaction (e.g., biological processing of the aspirated material, transfer of genetic material from the swatch to the biota in the aspirated material, etc.). By way of non-limiting example, the delivery element 25 can be any type of material/element that is able to contain the biological agents 31 and to selectively release them when desired. For example, the delivery element 25 can be a selectively permeable membrane, a dissolvable material, dehydrated bacteria, deposited plasmids, or encapsulated cells.

Similarly, FIG. 6B illustrates an alternative embodiment in which the delivery element 122 includes an energy source in the form of a chemical solution(s) housed within a secondary delivery element 29 such as a second syringe or ampoule. The secondary delivery element 29 can be disposed within the piston 12 of the device 10. The secondary delivery element 29 can be activated to deliver the chemical solution(s) to the materials to produce a useful reaction and/or a desired chemical and/or physical change in the material. While FIG. 6B illustrates a configuration in which the chemical solution(s) is delivered to the materials within the barrel 14, one skilled in the art will appreciate that the device can be modified to deliver chemical solution(s) to a target material external to the device.

FIGS. 7A and 7B are representations of further embodiments of the present device. Referring to FIG. 7A, the energy source 22 and delivery element 526 can be selected so as to be capable of emitting radioactive energy to the material before the material is expelled from the device 10. One skilled in the art will appreciate that the radioactive energy can be used for a variety of purposes, including use as a marker material. Alternatively, the radioactive energy can be used to sterilize, purify, or crosslink the syringe contents.

In the embodiment of FIG. 7B, the energy source 22 and the energy delivery element 626 may be selected so as to remove energy (i.e., heat) from the material. In such an embodiment, endothermic energy or cooling sources may be disposed within the piston 12 and coupled to the energy delivery element 626 in communication with the material.

Exposure of the delivery element 26 to the contents of the syringe barrel 14 can induce a desired chemical and/or physical reaction.

Figure 8B:
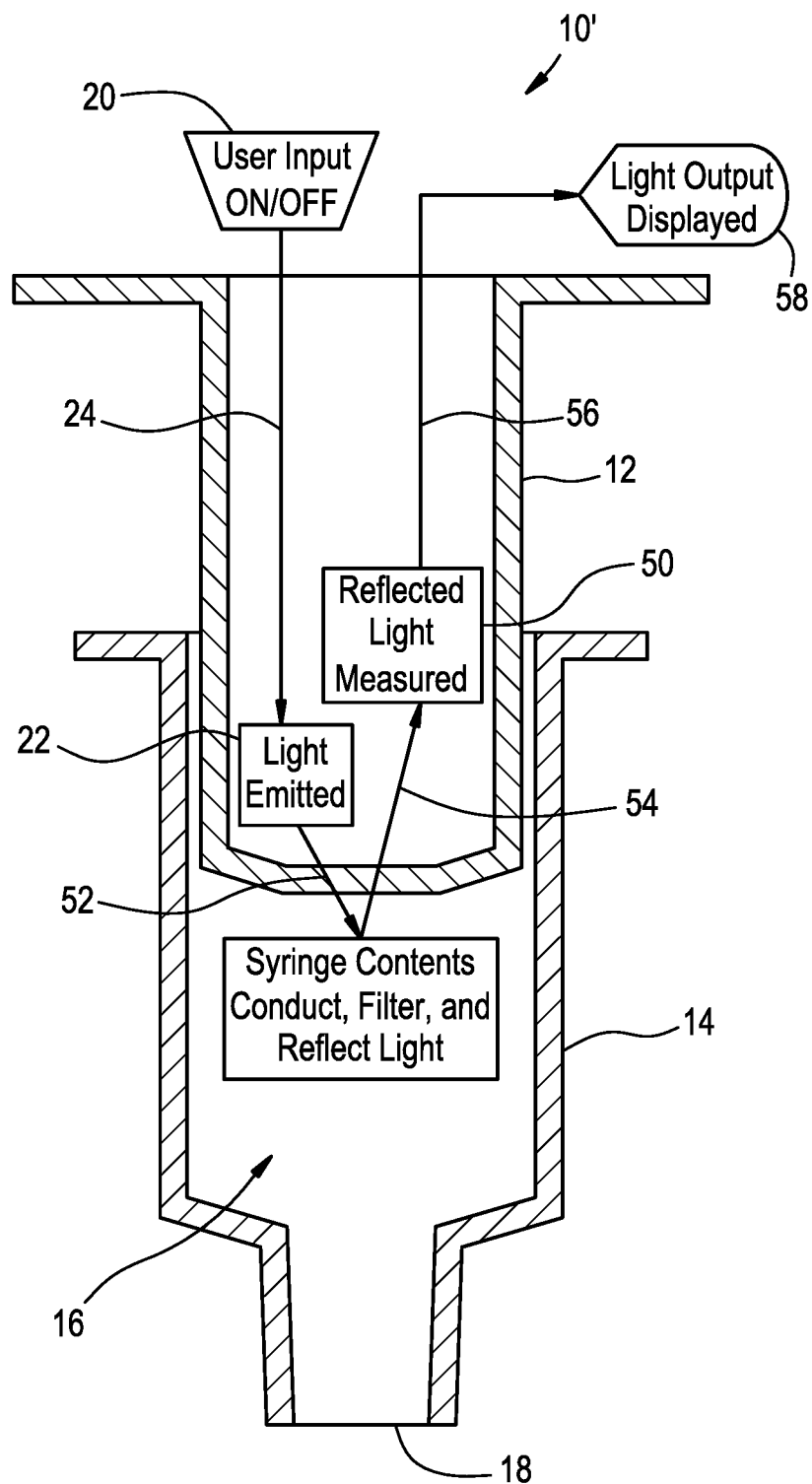
FIG. 8B is an alternative representation of the embodiment of FIG. 8A.

In addition to the various embodiments discussed above, additional components may be disposed within the device 10' in order to perform various functions. For example, FIGS. 8A and 8B schematically represent an embodiment wherein the device is adapted to perform a spectroscopic analysis on a material before it is expelled from the barrel 14. As shown, a detector 50 (e.g., photodiode, a CCD, a rheostat, a resistance or conductance meter or any other type of detector or transducer) can be disposed within the piston 12 to measure a response from the material following the delivery of energy from the source 22 to the material. In one embodiment, the energy source 22 can deliver a light energy to the material (as indicated by arrow 52) by way of a suitable delivery element (not shown). The material can produce a response such as a reflectance, fluorescence, luminescence, absorbance, etc. (as indicated by arrow 54) that is directed back to the detector 50, which is capable of measuring such response. Further, the detector 50 may be in communication (as indicated by arrow 56) with a display interface 58 capable of displaying the test results. In another embodiment, the detector 50 can be a chemi-luminescence detector wherein a light energy can be produced by the contents of the syringe barrel (e.g., light energy produced by an aspirated material) and detected by the detector 50.

The present invention is also applicable to methods for performing various procedures requiring the administration of energy and materials (e.g., therapeutic materials) to a treatment area. In general, the method can include aspirating a material into a syringe or syringe-like device, positioning the distal end of the syringe adjacent to a therapeutic treatment area, generating energy from an energy source disposed within the syringe, delivering the energy to a target via a delivery element either before or after the material is expelled from the syringe. Additionally, the target may be the actual treatment area (e.g., tissue, bone/tooth surface, etc.). As discussed in detail above, the method can include delivering a wide range of energies capable of producing various desired effects. Additionally, the method can include performing an analytical measurement by a detector disposed in the syringe prior to expelling the material from the syringe. While various embodiments are disclosed, those skilled in the art will recognize that any method utilizing the described syringe or syringe-like device is within the spirit and scope of the present invention.

The devices and methods of the invention are generally discussed herein in the context of a therapeutic system. One skilled in the art, however, will appreciate that the invention is equally applicable to a wide range of industrial applications. In general, the device can be used in any application requiring the production, delivery, and/or detection of energy via a syringe or syringe-like device. For example, the device can be utilized in adhesive dispensing processes (e.g., providing a desired amount of cross-linking and/or curing prior to dispensing) for electronics manufacture (among others). As another example, the device can be utilized for various types of sample testing such as ground water testing (e.g., sterilization and/or inactivation). These and other industrial applications are within the spirit and scope of the present invention.

The various embodiments discussed above are merely examples of energy sources, delivery elements, targets and/or desired effects capable of being utilized, targeted or produced by the device disclosed herein. Those skilled in the art will appreciate that a wide range of additional types of energy, delivery elements, targets, etc. are within the spirit and scope of the present invention. For example, the device 10 may include an electrical energy source capable of producing any type of electrical energy (AC, DC, pulsed, bipolar, monopolar, etc.) to an internal and/or external target in order to produce any desired effect. Further, all types and intensities of magnetic and electrostatic energy used to produce all types of effects are clearly within the spirit and scope of the present invention. Furthermore, those skilled in the art will appreciate that various individual elements discussed above may be combined with elements from other embodiments and remain within the spirit and scope of the present invention.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. A surgical method, comprising:
    positioning a device with respect to a target external to the device, the target comprising a treatment area, the device having a tubular outer component and an inner component movably disposed within the outer component, the inner component having a light energy source and a detector;
    using the light energy source, delivering light to the target;
    using the detector, measuring a response from the target resulting from the delivery of light to the target; and
    advancing the inner component relative to the outer component after measuring the response by the detector.

2. The method of claim 1, wherein the detector comprises a photodiode or a CCD.

3. The method of claim 1, wherein the light energy source comprises an ultraviolet or infrared emitter.

4. The method of claim 1, wherein the outer component has an open distal end.

5. The method of claim 1, wherein the inner component further comprises an optical waveguide configured to transmit the light emitted from light energy source to the target.

6. The method of claim 5, further comprising delivering at least a portion of the optical waveguide through a distal opening of the outer component to position the optical waveguide, such that the waveguide is configured to be adjacent to or in contact with the target.

7. The method of claim 1, further comprising illuminating the target, collecting reflected or refracted light from the target, and conducting a spectroscopic analysis of the target based on the reflected or refracted light.

8. The method of claim 1, wherein delivering light to the target comprises emitting the light through a distal end of the inner component.

9. The method of claim 1, wherein delivering light to the target comprises emitting the light along at least a portion of the length of the inner component.

10. The method of claim 1, further comprising performing a spectroscopic analysis of the target and displaying a result of the spectroscopic analysis on a display.

11. The method of claim 1, wherein advancing the inner component relative to the outer component is achieved using a handle formed at a proximal end of the inner component.

12. The method of claim 1, wherein the treatment area is within a patient's body.

13. The method of claim 1, wherein advancing the inner component relative to the outer component is achieved by driving a proximal end of the inner component in a distal direction.

14. A device, comprising:
a tubular outer component having an open distal end; and
an inner component movably disposed within the outer component, the inner component including a light energy source, an optical wave guide configured to transmit light emitted from the light energy source to a target external to the outer component, and a detector configured to measure a response from said external target resulting from the transmission of light thereto;
wherein at least a portion of the optical wave guide can selectively extend through the open distal end of the outer component such that the optical wave guide is configured to be positioned adjacent to or in contact with said external target.

15. The device of claim 14, wherein the detector comprises a photodiode or a CCD.

16. The device of claim 14, wherein the light energy source comprises an ultraviolet or infrared emitter.

17. The device of claim 14, further comprising a display that displays a result of a spectroscopic analysis of the target, the spectroscopic analysis being based on the response measured by the detector.

18. The device of claim 14, further comprising a handle formed at a proximal end of the inner component.

* * * * *